(12) United States Patent
Forssmann et al.

(10) Patent No.: US 7,033,997 B2
(45) Date of Patent: Apr. 25, 2006

(54) USE OF NATRIURETIC PEPTIDES AS ANTIBIOTICALLY ACTIVE SUBSTANCES FOR THE TREATMENT OF BACTERIAL INFECTIONS

(75) Inventors: Wolf-Georg Forssmann, Hannover (DE); Alexander Krause, Rinteln (DE); Erik Maronde, Hannover (DE)

(73) Assignee: Pharis Biotec GmbH, Hannover (DE)

( * ) Notice: Subject to any disclaimer, the term of this patent is extended or adjusted under 35 U.S.C. 154(b) by 19 days.

(21) Appl. No.: 10/989,397

(22) Filed: Nov. 17, 2004

(65) Prior Publication Data

US 2005/0089514 A1    Apr. 28, 2005

Related U.S. Application Data

(62) Division of application No. 10/069,128, filed as application No. PCT/EP00/08545 on Sep. 1, 2000, now abandoned.

(30) Foreign Application Priority Data

Sep. 3, 1999    (DE) ................................ 199 42 230

(51) Int. Cl.
*A01N 37/18*    (2006.01)
*A61K 38/00*    (2006.01)

(52) U.S. Cl. .......................................... 514/2
(58) Field of Classification Search .................. 514/2, 514/12, 13
See application file for complete search history.

(56) References Cited

FOREIGN PATENT DOCUMENTS

| | | |
|---|---|---|
| CA | CA 2188143 | 4/1994 |
| WO | WO 95/28952 | 11/1995 |

OTHER PUBLICATIONS

Hirohe, et al., C-Type Natriuretic Peptide Incr's Myocardial Contractility and Sinus Rate Med'd by Guanylyl Cyclase Linked Natriuretic Peptide Receptors in Isolated, Blood-Perfused Dog Hear Prep., The Jn. of Pharm. and Exp. Ther., 1998, 286(1) pp. 70-76.*
Webster's New World Dictionary, Third College Edition, 1988, p. 499.*
NutriBase Glossary: Fish, Poultry, and Mests, www.nutribase.com, printed Jun. 13, 2005, pp. 1-40.*
Dr. James Hill, Natriuretic Peptides in Heart Failure, Introduction, created May 7, 2001, modified Feb. 20, 2002, http://medinfo.ufl.edu/cme/grounds/hill/intro.html, printed Sep. 21, 2005, p. 1.*
Vollmar, et al., Effects of atrial natriuretic peptide on phagocytosis and respiratory burst in murine macrophages, European Journal Of Pharmacology, Vol. 319, 1997, pp. 279-285.

* cited by examiner

*Primary Examiner*—Bruce R. Campell
*Assistant Examiner*—Jennifer Ione Harle
(74) *Attorney, Agent, or Firm*—Jacobson Holman PLLC

(57) ABSTRACT

The present invention relates to antibiotically active natriuretic peptides for use as antibiotically active preparations prepared using biotechnological and recombinant methods and chemical synthesis. The antibiotically active peptides are referred to as natriubiotics. After chemical peptide synthesis, these natriubiotics can be used as human or veterinary medicaments in a suitable galenic formulation or as food additives.

9 Claims, 2 Drawing Sheets

Figure 3:
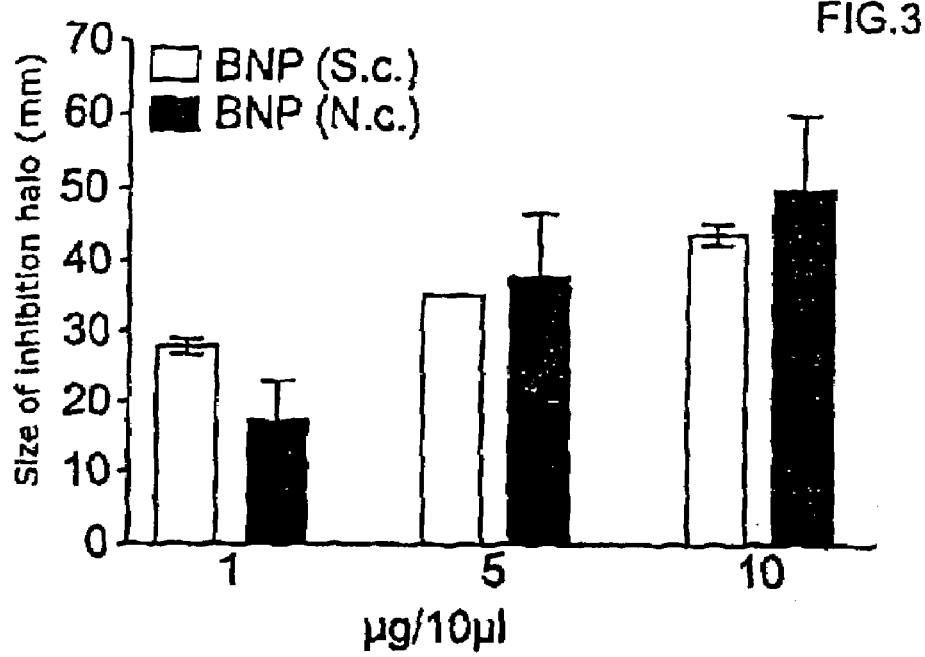

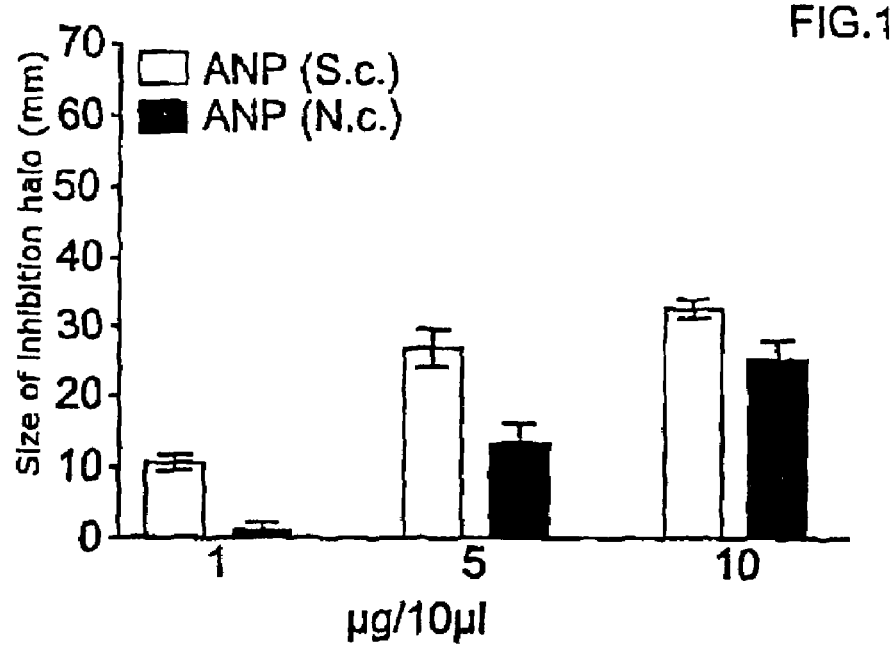
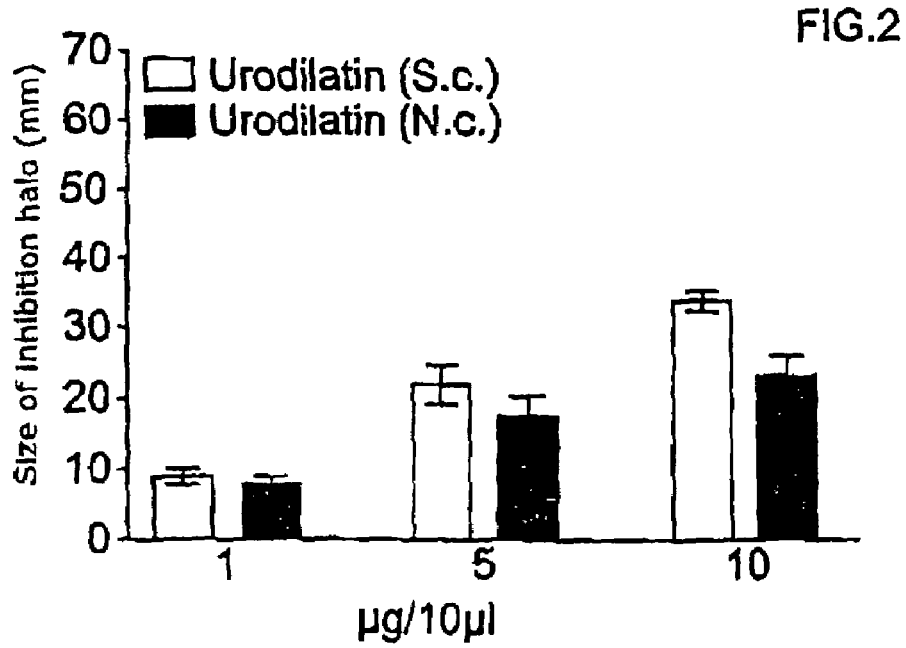

USE OF NATRIURETIC PEPTIDES AS ANTIBIOTICALLY ACTIVE SUBSTANCES FOR THE TREATMENT OF BACTERIAL INFECTIONS

This is a divisional of no. 10/069,128, filed Mar. 4, 2002, now abandoned which is a 371 of PCT/EP00/08545, filed Sep. 1, 2000, the disclosures of which are incorporated herein by reference.

The present invention relates to the use of natriuretic peptides (ANP, BNP, CNP and urodilatin) as antibiotically active peptide preparations. The peptides are obtained by chemical peptide synthesis or biotechnological production, and confectioning as a galenically prepared substance for medical and veterinary use as a medicament.

The peptides to which this invention relates are members of the family of natriuretic peptides. The primary structures of atrial natriuretic peptide (ANP) of rats (Flynn et al., 1983), pigs (Forssmann et al., 1983, 1984) and humans (Kangawa and Matsuo, 1984) have been described. The form of ANP which occurs in the kidneys, urodilatin, was first isolated in 1988 by Forssmann et al. (Schulz-Knappe et al., 1988). The homologue of atrial natriuretic peptide (ANP), the brain-type natriuretic peptide (BNP), was first isolated in 1988 by Sudoh et al. To date, an antibiotic activity of natriuretic peptides has not been suggested. To prove anti-microbial activity, a test is preferably performed which is suitable for basic peptides. A useful test for recognizing antibiotic activity is the growth inhibition test of Lehrer et al. (Lehrer et al. J. Immun. Methods, Vol. 137, p. 167, 1991).

It has been the object of the invention to provide antibiotically active agents. This object is achieved by the use of natriuretic peptides (natriubiotics, such as ANP, BNP, CNP and urodilatin) according to claim 1. The dependent claims relate to preferred embodiments of the use according to the invention.

According to the invention, the natriubiotics (i.e., natriuretic peptides) are used for the preparation of an antibiotically active agent for the treatment of a pathogenically altered bacterial flora in the gastro-intestinal tract, respiratory and urogenital systems, the skin, and for use in food technology as an auxiliary agent in fermenting processes and as a preservative.

When used as medicaments, the natriubiotics (i.e., natriuretic peptides) are preferably formulated in amounts of from 1 µg to 1 mg per unit into infusions, ointments, tablets, sprays or sustained release capsules.

The use of natriubiotics (i.e., natriuretic peptides) according to the invention also comprises the treatment of alterations of the intestinal flora, the treatment of microbially induced skin diseases, the treatment of aberrations of the human vaginal flora. The use of natriubiotics (i.e., natriuretic peptides) in food technology according to the invention also comprises the use as a preservative for foods or other perishable goods, as an auxiliary agent in industrial fermenting processes, e.g., in beer production, in yogurt production and in sauerkraut production.

Surprisingly, human ANP 99–126 and urodilatin have a growth-inhibiting effect on Gram-positive bacteria, such as B. subtilis, M. luteus and S. carnosus, and on Gram-negative bacteria, such as E. coli, N. cinerea and P. fluorescens, and the yeast S. cerevisiae. Also, human BNP-312 has the same growth-inhibiting effect on Gram-positive bacteria, such as B. subtilis, M. luteus and S. carnosus, and on Gram-negative bacteria, such as E. coli, N. cinerea and P. fluorescens, and the yeast S. cerevisiae. The growth-modulating property of these specific natriuretic peptides on certain germs has been unequivocally proven for the first time.

By chemical and biotechnological synthesis, the natriuretic peptides can be prepared in a highly pure and biologically active form and employed as a medicament.

The substances which can be used according to the invention, consisting of synthetic and recombinant products, can change the bacterial flora of the intestine, the skin and other bacterially colonized body zones and lead to an improvement of the germ flora in bacterial colonization by misplaced species. Therefore, the isolated pure substances can be used for controlling diarrheas, especially infant diarrheas, i.e., infections of the gastrointestinal tract, but also of the respiratory system, the urogenital system and in skin infections. The preparations can be used as additives for foods or as therapeutic agents and serve as auxiliary agents in the production of foods, especially in foods which are prepared by fermentation and other bacterial processes. These preparations are natural preservatives, In the following, the invention is illustrated by means of Examples and the following Figures to which reference is made in the Examples:

FIG. 1 shows a growth inhibition test of ANP

Radial diffusion growth inhibition test with *Streptococcus carnosus* and *N. cinerea* according to Lehrer et al. (Lehrer et al., J. Immun. Methods, Vol. 137, p. 167, 1991). The growth inhibition test is particularly suitable for the detection of antibiotic peptides since a special agarose which does not contain any fixed charged sites was used as the support material instead of the otherwise usual agar-agar. After application of 1 µg of ANP (both germs), inhibition halos can be observed.

FIG. 2 shows a growth inhibition test of urodilatin

Radial diffusion growth inhibition test with *Streptococcus carnosus* and *N. cinerea* according to Lehrer et al. (Lehrer et al., J. Immun. Methods, Vol. 137, p. 167, 1991). The growth inhibition test is particularly suitable for the detection of antibiotic peptides since a special agarose which does not contain any fixed charged sites was used as the support material instead of the otherwise usual agar-agar. After application of 1 µg of urodilatin (both germs), inhibition halos can be observed.

FIG. 3 shows a growth inhibition test of BNP-32

Radial diffusion growth inhibition test with *Streptococcus carnosus* and *N. cinerea* according to Lehrer et al. (Lehrer et al., J. Immun. Methods, Vol. 137, p. 167, 1991). The growth inhibition test is particularly suitable for the detection of antibiotic peptides since a special agarose which does not contain any fixed charged sites was used as the support material instead of the otherwise usual agar-agar. After application of 0.1 µg of BNP (both germs), inhibition halos can be observed.

Figure 4:
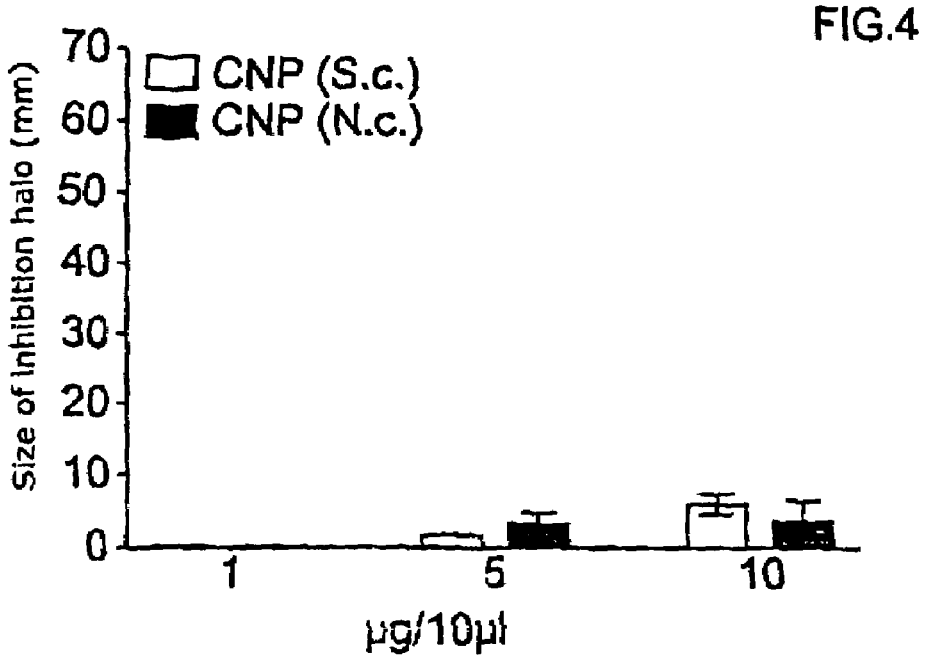

FIG. 4 shows a growth inhibition test of CNP

Radial diffusion growth inhibition test with *Streptococcus carnosus* and *N. cinerea* according to Lehrer et al. (Lehrer et al., J. Immun. Methods, Vol. 137, p. 167, 1991). The growth inhibition test is particularly suitable for the detection of antibiotic peptides since a special agarose which does not contain any fixed charged sites was used as the support material instead of the otherwise usual agar-agar. After application of 7 µg (*S. carnosus*) and 11 µg (*N. cinerea*) of CNP, inhibition halos can be observed.

EXAMPLE 1

Chemical synthesis of the antibiotically active peptides ANP, BNP, urodilatin and CNP Strategy of the synthesis of human natriuretic peptides:

For the synthesis of the peptides with the following sequences:

Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr (SEQ ID NO: 1) (ANP/CDD)

Ser-Phe-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys-Lys-Val-Leu-Arg-Arg-His (SEQ ID NO: 2) (BNP)

Gly-Leu-Ser-Lys-Gly-Cys-Phe-Gly-Leu-Lys-Leu-Asp-Arg-Ile-Gly-Ser-Met-Ser-Gly-Leu-Gly-Cys (SEQ ID NO: 3) (CNP)

Thr-Ala-Pro-Arg-Ser-Leu-Arg-Arg-Ser-Ser-Cys-Phe-Gly-Gly-Arg-Met-Asp-Arg-Jle-Gly-Ala-Gln-Ser-Gly-Leu-Gly-Cys-Asn-Ser-Phe-Arg-Tyr (SEQ ID NO: 4) (urodilatin), 1 the continuous flow method (Atherton and Sheppard, in "Solid Phase Peptide Synthesis", IRL Press, Oxford 1989) has been used. The peptide sequence mentioned is synthesized by means of an automated peptide synthesis apparatus (Minigen 9050) using Fmoc amino acids. The Fmoc amino acids had L-configuration and were employed in a fourfold excess.

The following amino acid derivatives were used for the synthesis: Fmoc-Lys (Boc), Fmoc-Arg (Pmc), Fmoc-His (Trt), Fmoc-Glu (OtBu), Fmoc-Ser(tBu), Fmoc-Gln(Trt), Fmoc-Leu, Fmoc-Phe, Fmoc-Ile, Fmoc-Val. Cys, Gly, Met and Asp are lacking.

The synthesis is performed with a C-terminal amino acid (0.091 mmol of alanine/g of resin) bound to Fmoc-L-Ala-PEG-PS support (Millipore). All coupling processes of amino acid derivatives were performed in the presence of O-(1H-benzotriazole-1-yl)-N,N–N',N'-tetramethyluronium tetrafluoroborate (TBTU), 1-hydroxybenzotriazole and diisopropylethylamine. The following synthesis cycles were used:

Fmoc deprotection with 20% piperidine in DMF for 10 min;

washing with DMF for 12 min;

acylation for 30 min;

washing with DMF for 8 min.

The synthesis is monitored by continuous UV detection. The synthesis is concluded with the cleavage of the N-terminal Fmoc residue. The resin-bound peptide is washed three times with 50 ml each of isopropanol, glacial acetic acid, isopropanol and diethyl ether, and dried.

The peptides are cleaved from the carrier resin by adding a mixture of TFA-ethanedithiol-water (94:3:3; v/v/v) and precipitated with ether.

The purification of the peptide is effected by reversed-phase HPLC using a C18 column (Vydac, 10 pmm 300 A, 20×250 mm, detection at 230 nm). The following mobile solvents were used: eluent A: 0.06% trifluoroacetic acid (TFA); eluent B: 0.06% TFA in acetonitrile/water (4:1). The flow rate is 10 ml/min, and the gradient is as follows: from 20% B to 80% B within 70 min. The pure fractions are pooled and lyophilized.

The purity and identity of the peptides is determined by mass spectrometry (quadrupole electrospray mass spectrometry, Sciex API 111, Perkin Elmer) and sequencing in a gas-phase sequencer (model 470, Applied Biosystems, Weiter-stadt) and checked by capillary zone electrophoresis. The biological activity is verified by the growth inhibition test.

EXAMPLE 2

Recombinant Preparation

The recombinant preparation is effected by usual methods, resulting in a similarly pure peptide for galenic use.

The invention claimed is:

1. A method of using a natriuretic peptide as an antibacterial agent comprising
  administering an effective amount of the natriuretic peptide to a patient in need thereof for treatment of pathogenically altered bacterial flora in the gastrointestinal tract, urogenital system, or the skin or
  adding the natriuretic peptide to food.

2. The method of claim 1 comprising administering the natriuretic peptide to a patient in need thereof for treatment of pathogenically altered bacterial flora in the gastrointestinal tract, urogenital system, or the skin.

3. The method of claim 2, wherein the natriuretic peptide is administered at 1 µg to 1 mg per unit dose.

4. The method of claim of claim 2 for the treatment of pathogenically altered bacterial flora in the gastrointestinal tract.

5. The method of claim of claim 2 for the treatment of pathogenically altered bacterial flora in the urogenital system.

6. The method of claim of claim 2 for the treatment of pathogenically altered bacterial flora in the skin.

7. The method of claim 1 comprising adding the natriuretic peptide to food.

8. The method of claim 7 wherein the natriuretic peptide is added to a food as a preservative.

9. The method of claim 7 wherein the natriuretic peptide is added to fermenting food for controlling bacterial growth during the fermentation.

* * * * *

SEQUENCE LISTING

<160> NUMBER OF SEQ ID NOS: 4

<210> SEQ ID NO 1
<211> LENGTH: 28
<212> TYPE: PRT
<213> ORGANISM: Homo sapiens

<400> SEQUENCE: 1

Ser Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr
            20                  25

<210> SEQ ID NO 2
<211> LENGTH: 32
<212> TYPE: PRT
<213> ORGANISM: Homo sapiens

<400> SEQUENCE: 2

Ser Phe Lys Met Val Gln Gly Ser Gly Cys Phe Gly Arg Lys Met Asp
 1               5                  10                  15

-continued

Arg Ile Ser Ser Ser Ser Gly Leu Gly Cys Lys Val Leu Arg Arg His
            20                  25                  30

<210> SEQ ID NO 3
<211> LENGTH: 22
<212> TYPE: PRT
<213> ORGANISM: Homo sapiens

<400> SEQUENCE: 3

Gly Leu Ser Lys Gly Cys Phe Gly Leu Lys Leu Asp Arg Ile Gly Ser
 1               5                  10                  15

Met Ser Gly Leu Gly Cys
            20

<210> SEQ ID NO 4
<211> LENGTH: 32
<212> TYPE: PRT
<213> ORGANISM: Homo sapiens

<400> SEQUENCE: 4

Thr Ala Pro Arg Ser Leu Arg Arg Ser Ser Cys Phe Gly Gly Arg Met
 1               5                  10                  15

Asp Arg Ile Gly Ala Gln Ser Gly Leu Gly Cys Asn Ser Phe Arg Tyr
            20                  25                  30